United States Patent [19]
Walker et al.

[11] Patent Number: 5,660,711
[45] Date of Patent: Aug. 26, 1997

[54] PROCESS FOR THE PREPARATION OF INTERMEDIATES USEFUL IN THE SYNTHESIS OF CEPHALOSPORINS

[75] Inventors: Derek Walker, Summit; Junning Lee, Gillette, both of N.J.; Charles R. Martin, Fort Collins, Colo.; Haiyan Zhang, Woodbury, Minn.; Loris Sogli, Novara; Ermanno Bernasconi, Caronno Varesino, both of Italy; Vinod Parakkal Menon, Fort Collins, Colo.

[73] Assignee: Schering Corporation, Kenilworth, N.J.

[21] Appl. No.: 569,631

[22] Filed: Dec. 8, 1995

Related U.S. Application Data

[63] Continuation-in-part of Ser. No. 353,030, Dec. 9, 1994, abandoned.

[51] Int. Cl.$^6$ .................................................. C25B 3/00
[52] U.S. Cl. ........................ 205/425; 205/426; 205/431; 205/435; 205/437; 205/441; 205/443; 205/445; 205/455; 205/456; 540/215
[58] Field of Search ................................. 205/425, 426, 205/431, 435, 437, 441, 443, 445, 455, 456; 540/215

[56] References Cited

U.S. PATENT DOCUMENTS

| | | | |
|---|---|---|---|
| 3,792,995 | 2/1974 | Ochiai et al. | 204/72 |
| 4,008,228 | 2/1977 | Chauvette | 260/243 |
| 4,042,472 | 8/1977 | Hall | 204/73 |
| 4,224,415 | 9/1980 | Meitzner et al. | 521/38 |
| 4,297,220 | 10/1981 | Meitzner et al. | 210/690 |
| 4,379,739 | 4/1983 | Hall | 204/72 |
| 4,634,697 | 1/1987 | Hamashima | 514/202 |

FOREIGN PATENT DOCUMENTS

| | | |
|---|---|---|
| 0082656 | 6/1983 | European Pat. Off. . |
| 0359540 | 3/1990 | European Pat. Off. . |
| 0 366 354 | 5/1990 | European Pat. Off. . |
| 0 420 562 | 4/1991 | European Pat. Off. . |
| 0556630 | 8/1993 | European Pat. Off. . |
| 2136154 | 12/1972 | France . |

OTHER PUBLICATIONS

Ochiai et al., "Electrochemical Reduction of cephalosporanic Acids", J. Chem. Soc., Perkins Trans., pp. 258–262. ? 1974.
Yoshioka, *Pure Appl. Chem.*, 59, 1041–1046 (1987) No month available.
Jones et al., *J. Pharm. Pharmac.*, 20 (Suppl.), 45S–47S (1968) No month available.
Hall *J. Pharm. Sci.*, 62 (6), 980–983 (1973).
Ochiai et al., *J. Chem. Soc., Perkins Trans.* I, 258–262 (1974) No month available.
Baldwin et al., *Tetrahedron*, 49 (22), 4907–4922 (1993) No month available.
Torii et al., *Bull. Chem. Soc. Jpn.*, 59, 3975–3976 (1986) No month available.
Torii et al., *Bull. Soc. Chim Belg.*, 91 (12), 951–965 (1982) No month available.
Hamashima et al., *J. Antiobiot.*, 40(10), 1468–1470 (1987) No month available.
Ochiai et al., *Tet. Lett.*, (23) 2341–2344 (1972) No month available.
Hall et al., *J. Electranal. Chem.*, 80, 155–170 (1977) No month available.
"Kirk–Othmer Concise Encyclopedia of Chemical Technology", John Wiley & Sons, New York, 843–844 (1985) No month available.
Walker, et al., J.C.S. Perkin I, 2030 (1975) No month available.
Chemical Abstracts, vol. 122 No. 17 (Apr. 24 1995), abstract No. 213854f.

*Primary Examiner*—Kathryn L. Gorgos
*Assistant Examiner*—Edna Wong
*Attorney, Agent, or Firm*—Joseph T. Majka; John H. C. Blasdale; Paul A. Thompson

[57] ABSTRACT

A process is described for preparing 3-exomethylene cephalosporanic acid derivatives for use in the synthesis of cephalosporin antibiotics such as ceftibuten. The process comprises electrochemical reduction of a compound of the formula (IV)

wherein: $R^3$ is $CH_3C(O)—$;

$\left(\begin{array}{c} O \\ \| \end{array}\right)$ is an optional sulfoxide group; n is 2 or 3; $R^1$ is H and R is H or $NHR^2$, where $R^2$ is H or a protecting group selected from $C_6H_5CH_2OC(O)—$, $C_6H_5C(O)—$ or $C_1$–$C_6$ alkoxy-C(O)—; or wherein R and $R^1$ together with the carbon atom to which they are attached comprise —C(O)—, and produces the desired 3-exomethylene compounds with low levels of the corresponding 3-methyl tautomers.

18 Claims, No Drawings

PROCESS FOR THE PREPARATION OF INTERMEDIATES USEFUL IN THE SYNTHESIS OF CEPHALOSPORINS

CROSS-REFERENCE TO RELATED APPLICATION

This application is a continuation-in-part of U.S. patent application Ser. No. 08/353,030 filed Dec. 9, 1994, now abandoned, by Walker et al.

The present invention provides a process for preparing intermediates useful in the synthesis of cephalosporin type antibiotics.

BACKGROUND OF THE INVENTION

U.S. Pat. No. 4,634,697 describes cephalosporin compounds including Ceftibuten, a commercially important third generation cephalosporin type antibiotic having the chemical formula (I)

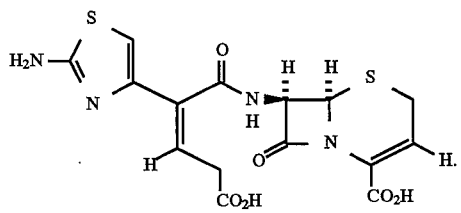

The synthesis of ceftibuten starting from penicillin G is described in Yoshioka, *Pure Appl. Chem.*, 59, 1041 (1987). However, this process is costly and inefficient leaving a current need for a more cost effective and efficient process for the commercial scale preparation of ceftibuten.

The electrochemical transformation of derivatives of cephalosporin C is known. See, Jones, et al, *J. Pharm. Pharmac.*, 20, (Suppl.) 45S–47S (1968), and Hall, *J. Pharm. Sci.*, 62, (6) 980–983 (1973). The formation of 3-exomethylene cephalosporins via electrochemical reduction is described in Ochiai, et al., *J. Chem. Soc., Perkin Trans. I*, 258–262 (1974) and U.S. Pat. Nos. 3,792,995 and 4,042,472. Baldwin, et al., *Tetrahedron*, 49, (22) 4907–4922 (1993), also describes the electrochemical reduction of cephalosporin C to form an 3-exomethylene compound of the formula

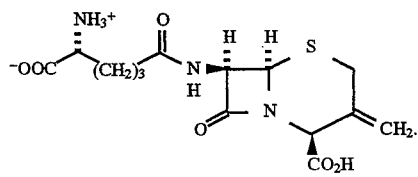

In addition, EP 082,656 describes the electrochemical reduction of acetoxymethyl compounds of the formula

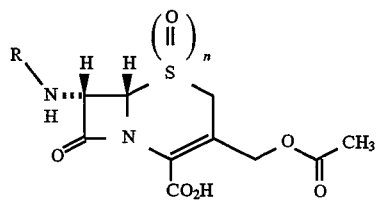

wherein n is 0 or 1, and R is H or an acyl group, to form the corresponding 3-exomethylene compounds.

The electrochemical processes described above are chemically inefficient, requiring dilute reaction concentrations, low current densities and often producing low yields. Moreover, the prior art processes typically produce significant levels of the 3-methyl tautomer of the desired 3-exomethylene compounds. These 3-methyl compounds are essentially useless for the synthesis of cephalosporin type antibiotics and are difficult to remove from the desired 3-exomethylene product. As a result, 3-exomethylene compounds prepared via the prior art electrochemical processes are unsuitable for use in the manufacture of cephalosporin drugs. Consequently, in spite of the potential advantages of electrochemical processes, such as environmental cleanliness and safety, not one is suitable for development into a commercial scale process. There is therefore a need for robust and efficient electrochemical process which will reliably produce 3-exomethylene cephalosporins in high yield and with low levels (i.e., less than 5%) of 3-methyl tautomers.

SUMMARY OF THE INVENTION

The present invention solves the problems of the prior art processes by providing an efficient electrochemical process for preparing 3-exomethylene cephalosporins while producing very low levels of the 3-methyl tautomer. More specifically the present invention provides a process for preparing compounds of the formula (II) or (III) and esters thereof

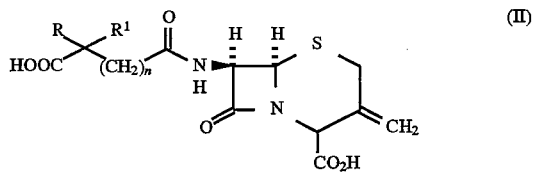

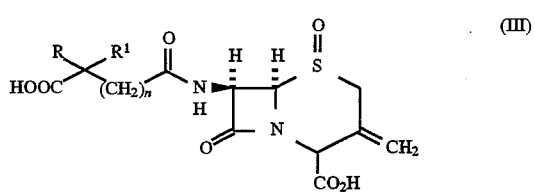

wherein: n is 2 or 3; $R^1$ is H and R is H or $NHR^2$, where $R^2$ is H or a protecting group selected from $C_6H_5CH_2OC(O)$—, $C_6H_5C(O)$— or $C_1$–$C_6$ alkoxy-C(O)—; or wherein R and $R^1$ together with the carbon atom to which they are attached comprise —C(O)—. Compounds (II) and (III) and the esters thereof are useful as intermediates in the synthesis of ceftibuten (I).

The process of the present invention comprises electrochemically reducing a solution of a compound of the formula (IV)

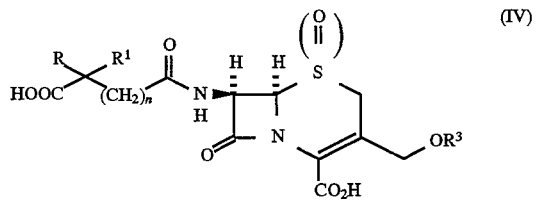

wherein: $R^3$ is $CH_3C(O)$—;

$$\left(\overset{O}{\underset{\parallel}{}}\right)$$

is an optional sulfoxide group; and n, R and $R^1$ are as defined above, at a concentration of 10–50 g/L, at a pH of 7–10, and at a current density of 10–150 mA/cm², in the presence of a buffer and in a solvent selected from water, an organic solvent, or a mixture of water and a water miscible organic additive, to form a compound of the formula (II) or (III).

The present invention also provides novel compounds of the formula (II) or (III) as defined above, wherein n is 2 or 3; $R^1$ is H and R is H or $NHR^2$, where $R^2$ is $C_6H_5C(O)$—; $C_6H_5CH_2OC(O)$—, or $(CH_3)_2CHCH_2OC(O)$—; or wherein R and $R^1$ together with the carbon to which they are attached comprise —C(O)—, and esters or salts thereof.

In an alternative embodiment, the present invention provides a process for preparing compounds of the formula (V)

(V)

wherein $R^4$ is diphenylmethyl, and n, $$\left(\overset{O}{\underset{\parallel}{}}\right),$$

R and $R^1$ are as defined above. In this embodiment the process of the present invention comprises:

(a) electrochemically reducing a compound of the formula (IV), as defined above, to form a compound of the formula (II) or (III), as defined above, followed by chromatographic purification of the electrochemical reduction product on an adsorbent resin;

(b) esterifying the compound of formula (II) or (III) from step (a) to form a compound of the formula (VI)

(VI)

wherein $R^4$ is diphenylmethyl, and n, $$\left(\overset{O}{\underset{\parallel}{}}\right),$$

R and $R^1$ are as defined above; and (c) ozonolyzing the compound (VI) from step (b) to form a compound of the formula (V), as defined above.

The present invention further provides a process for preparing the diphenylmethyl ester of 7-amino-3-desacetoxymethylcephalosporanic acid, i.e., a compound of the formula (VII)

(VII)

wherein $R^4$ is diphenylmethyl, comprising the steps:

(d) reducing a compound of the formula (V) as defined above to form a compound of the formula (VIII)

(VIII)

wherein $R^4$, n, R, $$\left(\overset{O}{\underset{\parallel}{}}\right)$$

and $R^1$ are as defined above;

(e) reacting the product of step (d) with a compound of the formula P-X, wherein P is a sulfonyl activating group and X is Cl, Br or I, in the presence of a tertiary amine base to form a compound of the formula (IX)

(IX)

wherein P is a sulfonyl activating group, and $R^4$, n, $$\left(\overset{O}{\underset{\parallel}{}}\right),$$

R and $R^1$ are as defined above; and (f)
  (i) treating the product of step (e) with $PCl_5$ in the presence of a tertiary amine base and an alcohol or diol, then with a dialkylamine base; or
  (ii) treating the product of step (e) with a dialkylamine base or a tertiary amine base, and then with $PCl_5$ in the presence of a tertiary amine base and an alcohol or diol; and where an optional $$\left(\overset{O}{\underset{\parallel}{}}\right)$$

group is present treating with $PCl_3$; to form a compound of the formula (VII). Compound (VII) is a key intermediate in the commercial synthesis of ceftibuten (I).

DETAILED DESCRIPTION

The publications cited and referred to herein are hereby incorporated by reference in their entirety.

As used herein, the term:

"alkyl" means a straight or branched alkyl chains of 1 to 6 carbon atoms;

"aryl" means a $C_6-C_{10}$ carbocyclic aromatic group, such as phenyl or naphthyl; and "substituted aryl" means an aryl group having 1 to 3 substituents selected from halogeno, $C_1-C_6$ alkyl, $NO_2$ or $CF_3$;

"halogeno" means Cl, Br or I;

"sulfonyl activating group" means a substituent of the formula —$SO_2R^6$, wherein $R^6$ is $C_1-C_6$ alkyl, aryl, substituted aryl or —$CF_3$;

"hydride reducing agent" means $NaBH_4$, $LiBH_4$, $NaBH_3CN$, or a combination of $NaBH_4$ and LiCl;

"aqueous acid" means an aqueous solution of an acid, such as HCl;

"dialkylamine base" means a compound of the formula $HN(alkyl)_2$, such as diethylamine;

"tertiary amine base" means bases such as pyridine, DMAP, DMA, $Et_3N$ or Hünigs base;

"tetra(alkyl)ammonium salts" mean salts comprising a tetra(alkyl)ammonium cation, such as tetraethylammonium, tetraethylammonium, tetrabutylammonium or tetrapropylammonium, and a suitable counterion such as p-toulenesulfonate or sulfate;

"alcohol" means a $C_1-C_4$ alcohol, such as methanol, ethanol or i-propanol; and "diol" means a $C_2-C_6$ diol, such as ethylene glycol, 1,3-propanediol or 1,3-butanediol.

"Buffer" means one or more buffer compounds which are water soluble acids and/or bases, such as $LiH_2PO_4$, $KH_2PO_4$, $NaH_2PO_4$, $Li_2HPO_4$, $K_2HPO_4$, $Na_2HPO_4$, $Li_3PO_4$, $K_3PO_4$, $Na_3PO_4$, $LiHCO_3$, $NaHCO_3$, $KHCO_3$, $Na_2CO_3$, $K_2CO_3$, $Li_2CO_3$, NaOH, KOH, LiOH, $HClO_4$ and $H_3BO_3$, or salts, including borates (such as lithium borate, potassium borate, cesium borate or sodium borate) and quaternary ammonium salts, such as tetra(alkyl)ammonium salts. The buffer is an individual buffer compound, or two or more such compounds in combination, and is used to maintain constant pH and to facilitate the course of the eletrochemical reduction.

"Water miscible organic additives" are organic compounds which are soluble in water and relatively unsusceptible to electrochemical reduction under the conditions of the present invention, such as EtOAc, iPrOAc, $CH_3CN$, MeOH, EtOH, iPrOH, DMF, formamide, DMSO or urea.

"Adsorbent resin" means a polymeric nonionic macroreticular (i.e., porous) adsorbent capable of selectively adsorbing hydrophobic molecules, such as compounds of the formula (II), (III), (XII), (XIII) and (XIV), from a polar solvent, such as water. Such resins are typically aromatic polymers, such as styrene and divinylbenzene copolymers, which may be cross-linked. Such resins are known and are generally prepared by polymerization of the appropriate monomers. (See, e.g. U.S. Pat. Nos. 4,224,495 and 4,297,220) A number of such adsorbent resins are readily commercially available, including: Amberlite® XAD-7, XAD-1180, XAD-16 and XAD-1600 (available from Rohm & Haas); XUS-40323.00, XUS-40285.00 and XUS-40283.00 (available from Dow Chemical Co.); and Diaion HP 10, HP 20, HP 30, HP 40 and HP 50 (available from Mitsubishi Chemical).

As used herein the following reagents and solvents are identified by the abbreviations indicated: methanol (MeOH); tetrahydrofuran (THF); diethyl ether ($Et_2O$); t-butyl methyl ether (TBME); triethylamtne ($Et_3N$); di-isopropylethylamine (Hünigs base); ethyl acetate (EtOAc); iso-propylacetate (iPrOAc); acetic acid (HOAc); ethanol (EtOH); N,N-dimethylformamide (DMF); dimethylsulfoxide (DMSO); 4-dimethylaminopyridine (DMAP); N,N-dimethylaniline (DMA); p-toluenesulfonyl chloride (tosyl chloride or TsCl); methanesulfonyl chloride (mesyl chloride or MsCl); p-toluenesulfonic acid (p-TSA); isopropanol (iPrOH).

The present invention comprises a process for preparing a compound of the formula (II) or (III) as shown in Reaction Scheme 1

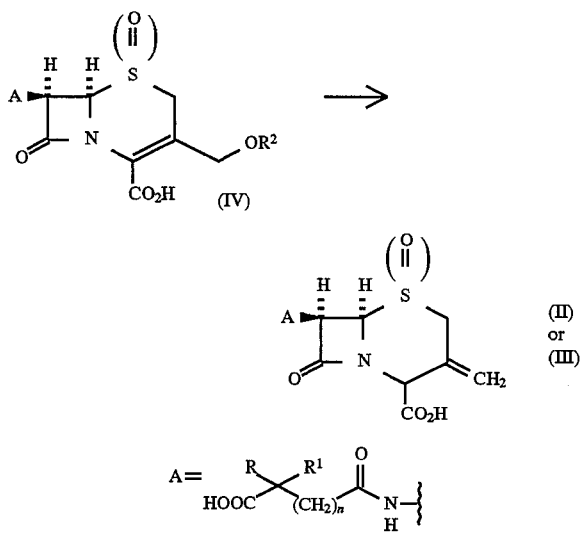

In Reaction Scheme 1, a solution comprising a compound of the formula (IV), as defined above, a suitable solvent, and a buffer, is electrochemically reduced to form a compound of the formula (II) or (III) as defined above. The working electrode (cathode) for this reduction is selected from known electrode materials so that hydrogen overpotential is maximized, and includes electrodes made from Ti, In, Cd, Pb, Ga, Zn, Ag, Sn, Bi, Hg, Pt, Mo, Nb, Ta, C, Cu, Fe and Ni, as well as metal alloys such as Pb/Ag, Cu/Hg and steels of various compositions, including those steels described in "Kirk-Othmer Concise Encyclopedia of Chemical Technology", pp. 1101–1105, John Wiley & Sons, New York (1985). Preferred cathode materials include Ti, In, Cd, Hg, Pb, Ga, Zn, Ag, Sn, Bi and C (in particular C in the form of graphite, graphite felt or reticulated vitreous carbon). Also preferred are cathodes made from C, Pb, Hg, Sn or Zn, with mercury, tin and lead being most preferred. Preferably the cathode has a high surface area such that the ratio of electrode area to solution volume is optimized. The reduction is preferably carried out at a current density of 10 $mA/cm^2$ to 150 $mA/cm^2$. The solvent is selected from water, a suitable organic solvent, or a mixture of water and a water miscible organic additive, and is preferably water or a mixture of water and a water miscible organic additive.

The electrochemical reduction is carried out at a temperature of −60° to 80° C., preferably at −20° to 30° C., more preferably at −20° to 20° C., and most preferably at 0° to 10° C., at a pH of 7–10. A buffer, or a combination of two or more buffers, is used as needed to maintain the desired pH range. The buffer is present at a concentration of 0.1M to 2M, preferably at 0.2M to 1.5M, and most preferably at 0.5M to 1.0M. The initial concentration of the starting compound (IV) in the reduction solution is from 1 g/L to 100 g/L, preferably at 10 g/L to 80 g/L and most preferably at 10 g/L to 50 g/L.

The electrochemical reduction is carried out in a suitable electrochemical cell, a large variety of which are known in the art. Preferably the cell is a flow cell wherein the solution comprising the compound to be reduced is circulated through the electrochemical cell from an external reservoir. Also preferred is a two-chambered cell wherein the cathode and anode are contained in separate chambers. The cathode and anode chambers of such cells are constructed such that fluid contained in one chamber is physically separated from the other chamber by a suitable divider while maintaining an electrical connection between the chambers. Preferably the divider is a porous material, such as sintered glass, or a suitable ion exchange membrane, such as a Nafion® membrane. The chamber containing the anode will also contain a solution of a buffer in water, which buffer can be the same or different as the buffer in the cathode chamber. Preferably the buffer in the anode chamber, i.e., the anolyte, is a phosphate salt, perchloric acid or sulfuric acid, with perchloric acid being preferred. The anolyte concentration is preferably 0.2M to 2M, and is most preferably about 1M.

Compounds of the formula (II), (III) and (IV) contain two carboxylic acid groups and therefore exist as anionic species at the preferred pH used for the electrochemical reduction. An ion exchange membrane divider, which is permeable to cations but not anions, can therefore be used to prevent migration of compounds (II), (III) and (IV) to the anode, thereby preventing the possibility of side reactions from occurring at that electrode. Preferably the ion exchange membrane is a perfluorinated ionomer membrane, such as the perfluorinated sulfonic acid or perfluorinated carboxylic acid ionomers described in the "Kirk-Othmer Concise Encyclopedia of Chemical Technology", John Wiley & Sons, p. 843–844 (New York, 1985), herein incorporated by reference. Most preferred are Nafion® or Flemion® membranes, with Nafion® membranes being especially preferred.

Compounds of the formula (IV) are known and can be readily prepared via established methods.

The product compounds (II) and (III) from the electrochemical reduction of Reaction Scheme 1 typically contain several byproducts as impurities. For Example, electrochemical reduction of a compound of formula (I) having the structural formula (L1)

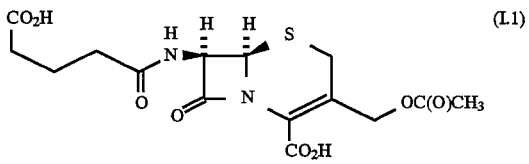

via the procedure described above produces a compound of the formula (II) having the structural formula (II.1)

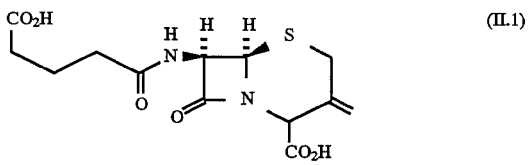

along with varying mounts of byproducts of the formulae (XII), (XIII) and (XIV).

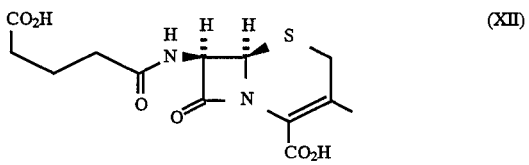

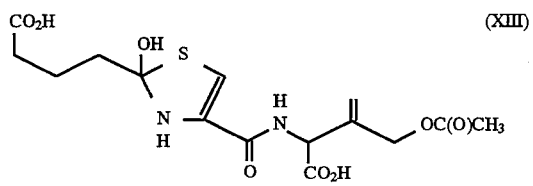

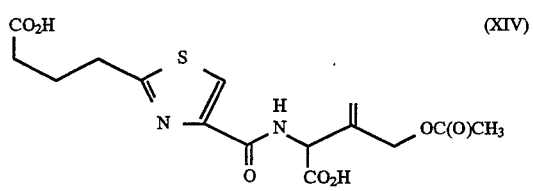

Purified 3-exomethylene products (II) and (III) offer a number of advantages (including superior performance in subsequent steps of the processes described in Reaction Schemes 2 and 3, below). An efficient method for removal of all, or at least some, of the byproducts from the desired reduction product (II) or (III) is therefore desirable. The instant invention also provides a method for removal of such byproducts comprising chromatography of the crude electrochemical reduction product on a suitable adsorbent resin. Examples of such resins include Amberlite® XAD-16, Amberlite® XAD-1180, Amberlite® XAD-7, Amberlite®XAD-1600, Dianon HP-20, SP-825, XUS-40323.00, XUS-40285.00, and XUS-40283.00, with XAD-16, XAD-1600, XAD-7, HP-20 and XUS-40323 being preferred. Most preferred for removing byproduct impurities of the formula (XII), (XIII) and (XIV) from a compound of the formula (II.1) is the adsorbent resin XAD-1600.

Adsorbent resin chromatography of the electrochemical reduction product is typically carried out at a temperature of 0° C. to 25° C. at a column load of about 30 g material/L of resin. The column is preconditioned by washing with methanol followed by deionized water. The electrolytic reduction solution containing the materials to be separated, obtained as described above, is filtered through a filter aid (such as celite®) then acidified to a pH of 3.5–4.0, and passed through the column, typically at a rate of about 1 column bed volumes/hour (BV/hr.) to load the column. The column is then eluted using a suitable solvent, such as deionized distilled water or a mixture of deionized distilled water and an alcohol (such as methanol, ethanol or isopropanol), which elution solvent may also contain a buffer to adjust the pH of the solution. The desired compound of formula (II) or (III) is obtained by lyophilization of the appropriate chromatography fractions.

The present invention also provides a process for preparing compounds of the formula (V) as shown in Reaction Scheme 2.

Reaction Scheme 2

Step A

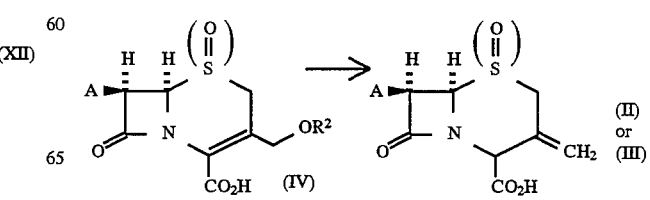

-continued
Reaction Scheme 2

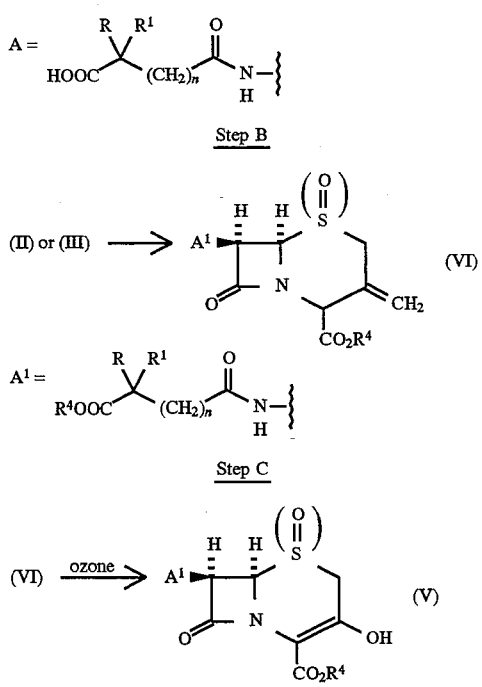

Reaction Scheme 3
Step D

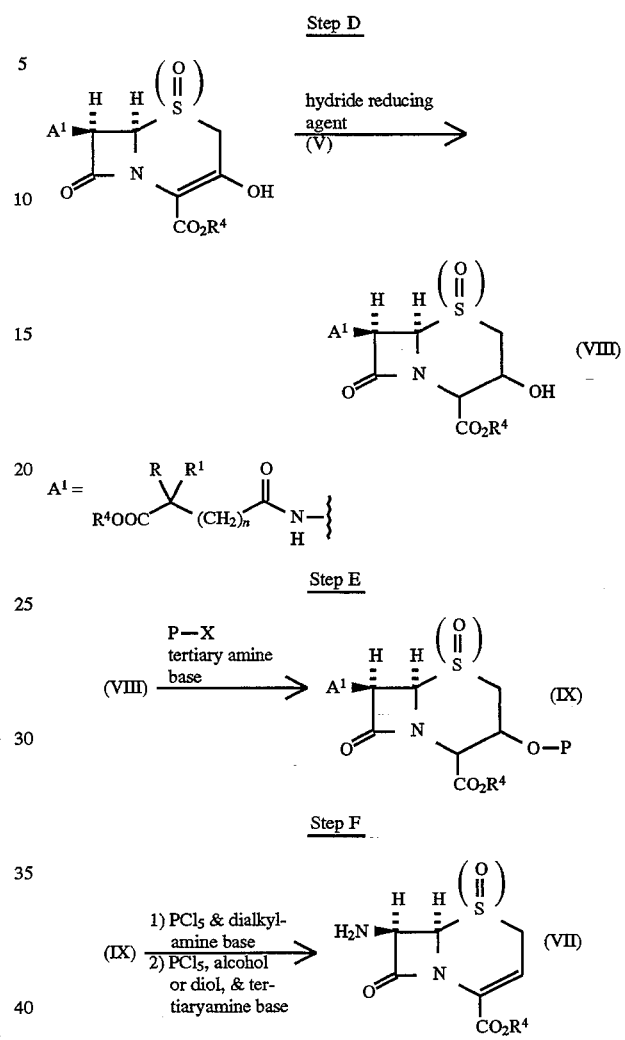

In Step A of Reaction Scheme 2 the starting compound (IV), as defined above, is electrochemically reduced to a compound of the formula (II) or (III) via the same procedure described for Reaction Scheme 1. The reduction product (II) or (III) is optionally purified by chromatography on an adsorbent resin as described above.

In Step B, a compound of the formula (II) or (III) is esterified by treating with a suitable esterifying agent, such as diphenyldiazomethane, in a suitable solvent, such as water or a mixture of water and a polar organic solvent, to form the diester (VI), as defined above.

In Step C, the diester (VI) is treated with ozone in a suitable solvent, such as $CH_2Cl_2$, at a temperature of $-100°$ C. to $0°$ C., preferably at $-80°$ to $-20°$ C., to form an ozonide intermediate, then further treated with a suitable reducing agent, such as $P(OC_2H_3)_3$ to reduce the ozonide intermediate and form a compound of the formula (V), as defined above.

In an alternative embodiment, the product (II) or (III) of Step A is treated with ozone, using essentially the same procedure as described for Step C (above), to form a compound of the formula (X)

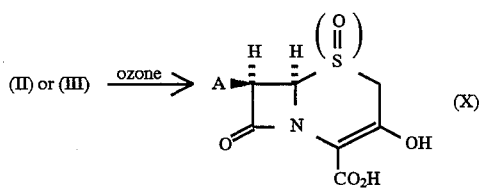

wherein A is as defined above, and the product (X) esterified using essentially the same procedure as described for Step B (above) to form a compound of the formula (V), as defined above.

The present invention further provides a process for preparing compounds of the formula (VII) as shown in Reaction Scheme 3.

In Reaction Scheme 3, step D, a compound of the formula (V), as defined above, is treated with a hydride reducing agent, preferably $NaBH_4$, in the presence of a suitable solvent to form a compound of the formula (VIII), wherein n, R, $R^1$, $R^4$ and

are as defined above. Suitable solvents include $Et_2O$, THF, a $C_1$–$C_4$ alcohol, water, a mixture of $CH_2Cl_2$ and a $C_1$–$C_4$ alcohol, or a mixture of water and a $C_1$–$C_4$ alcohol. The reaction is carried out at a temperature of $-100°$ C. to $30°$ C., preferably at $-80°$ C. to $0°$ C., and the specific solvent or solvent mixture to be used is selected such that the reaction temperature is higher than the freezing point of the mixture. Preferably the solvent is a mixture of $CH_2Cl_2$ and a $C_1$–$C_4$ alcohol and the reaction temperature is $-80°$ to $-40°$ C.

Steps E and F of Reaction Scheme 3 are carried out as a "one pot" process, i.e., the required reagents are sequentially added to the reaction mixture without workup or isolation between steps.

In Step E, the product (VIII) of step D is reacted with a compound of the formula P-X, wherein P and X are as defined above, in a suitable solvent, such as $CH_2Cl_2$, in the presence of a tertiary amine base, such as Et$_3$N, to form a mixture comprising a compound of the formula (IX), wherein P, R$^3$, n,

,

R and R$^1$ are as defined above, and a tertiary amine base.

In step F, the product mixture from step E is treated sequentially with PCl$_5$ and a dialkylamine base, such as diethylamine, to form a compound of formula (VII). Treatment with PCl$_5$ in the presence of the tertiary amine base and a C$_1$–C$_4$ alcohol, preferably methanol, or a C$_2$–C$_6$diol, preferably 1,3-butanediol, serves to cleave the amide side chain to form the free amino group. Additional tertiary amine base is added with the PCl$_5$ in step F as necessary. Treatment with dialkylamine base results in elimination of the 3-OP group to form the 3,4 double bond.

The reaction is carried out by adding PCl$_5$ and an alcohol or diol to the mixture, followed by treatment with a dialkylamine base. Alternatively the mixture is first treated with the dialkylamine base followed by treatment with PCl$_5$ and alcohol or diol.

Where an optional

group is present, step F further comprises treatment with PCl$_3$ to reduce the sulfoxide group to the analogous sulfide.

Compounds of the formula (VII) are readily converted to ceftibuten (I) via known methods.

In an alternative embodiment, the product (X) described above is treated with a hydride reducing agent, using essentially the same procedure as described for Step D (above) to form a compound of the formula (XI)

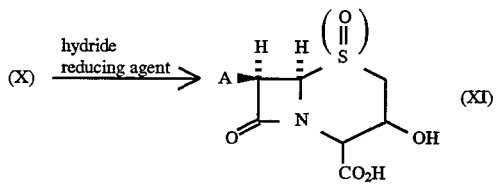

wherein A is as defined above, and the compound (XI) esterified via essentially the same procedure as described in Step B of Reaction Scheme 2 (above) to form a compound of the formula (VIII), as defined above. The compound (VIII) is then converted to a compound of the formula (VII) via the procedures described for Steps E and F (above).

The following preparations and examples are illustrative of the process of the present invention.

EXAMPLES

Materials and General Methods

Electrochemical reductions are carried out in an electrochemical cell with the counter electrode (anode) separated from the working (cathode) and reference electrodes. The potential can be controlled using a constant voltage source, such as a Princeton Applied Research Model 273 potentiostat, at from −1 to −3 volts, preferably from −1.5 to −2.5 volts.

Nafion® membranes for use as dividers are commercially available from a number of sources, e.g. DuPont or Aldrich Chemical Company. The Nafion® membrane is cleaned prior to use by boiling in 3% H$_2$O$_2$ for 30 minutes, followed by immersion in a hot (80° C.) solution of 9M nitric acid for 15 minutes. The membrane is then rinsed in boiling water, sonicated in several aliquots of hot (90° C.) water and stored under distilled water until needed.

The counter electrode is a platinum mesh electrode and the reference electrode is an Ag/AgCl electrode. The working electrode is a mercury pool (triple-distilled mercury) electrode; graphite (Johnson Mathey, 99.9995%) electrode; glassy carbon electrode, lead (Johnson Mathey 99.9999%) electrode, tin foil electrode (Aldrich 99.9% pure), or zinc (Johnson Mathey, 99.95%) rod sealed in Teflon®.

HPLC analysis is performed on a Brownlee HPLC Analytical Column (RP 18 SPHER I-5, 250×4.6 mm) maintained at a temperature of 35° C. The mobile phase is typically 94:6 0.025M KH$_2$PO$_4$ (aqueous)/CH$_3$CN at a flow rate of 1 mL/min., and a UV detector (225 nm) is used.

EXAMPLE 1

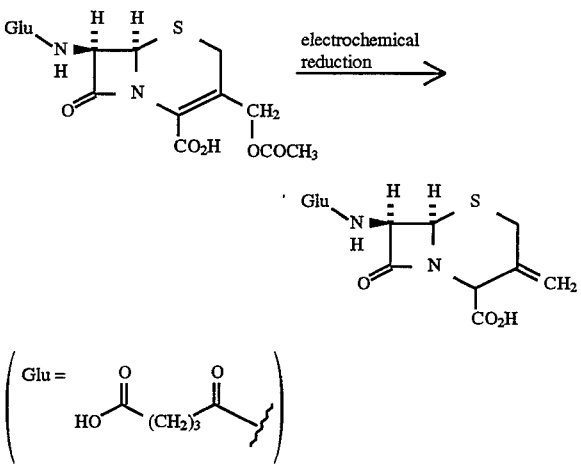

Dissolve 0.3 g of 7-glutaroyl 7-aminocephalosporanic acid (glutaroyl 7-ACA) in 30 mL of a pH 6.9 aqueous buffer solution of 0.1M KH$_2$PO$_4$, 0.1M Na$_2$HPO$_4$ and 0.018M NaHCO$_3$. Electrolyze the solution at room temperature using a mercury pool working electrode at a potential of −2.2 V for a period of 13 hours to give a 8.5:1 mixture of the exomethylene product and a 3-methyl compound of the formula

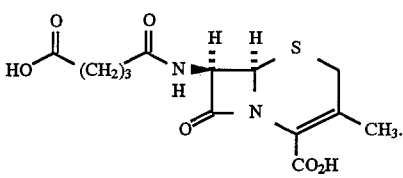

EXAMPLE 1A

Dissolve 0.3 g of glutaroyl 7-ACA in 30 mL of an aqueous buffer solution of 1M H$_3$BO$_3$ and add NaOH to adjust to pH 8.0. Electrolyze as described for Example 1 at a potential of −2.3 V for a period of 4¾ hours to give a 6.8:1 mixture of the same compounds as for Example 1.

EXAMPLE 2

Prepare an aqueous electrolysis solution of glutaroyl 7-ACA; 0.05M KH$_2$PO$_4$; 0.05M Na$_2$HPO$_4$; 0.08M boric acid; and 0.018M NaHCO$_3$. Record the initial pH of the solution and electrolyze as described for Example 1 at a potential of −2.2 V. Record the final pH and analyze by HPLC, as described above, to determine the yield and the ratio of 3-exomethylene to 3-methyl compound in the product mixture. Using the starting concentration of 7-glutaroylcephalosporanic acid indicated, the following results are obtained:

| Concentration of glutaroyl 7-ACA | Yield of exomethylene product | pH initial | pH final | Ratio 3-exo / 3-methyl |
|---|---|---|---|---|
| 1 g/L | 52% | 7.3 | 8.5 | 9.5:1 |
| 5 g/L | 50% | 6.8 | 8.9 | 10.1:1 |
| 10 g/L | 43% | 6.3 | 8.5 | 10.6:1 |

EXAMPLE 3

Prepare an aqueous electrolysis solution of 5 g/L of glutaroyl 7-ACA and 0.2M boric acid. Add NaOH to adjust the initial pH of the solution. Using a 2-chambered cell separated by a divider, electrolyze the solution as described for Example 1 at a potential of −2.2 V. Record the final pH and analyze by HPLC, as described above, to determine the yield and the ratio of 3-exomethylene to 3-methyl compound in the product mixture. At the reaction temperature indicated, the following results are obtained:

| Reaction Temp. | Divider material | Yield of exomethylene product | pH initial | pH final | Ratio 3-exo / 3-methyl |
|---|---|---|---|---|---|
| 25° C. | sintered glass | 49% | 8.3 | 9.4 | 10.4:1 |
| 25° C. | Nafion ® | 64% | 8.3 | 9.3 | 10.6:1 |
| 0° C. | Nafion ® | 67% | 8.7 | 8.3 | 13.5:1 |

EXAMPLE 4

Prepare an aqueous electrolysis solution of 10 g/L of glutaroyl 7-ACA and 0.5M boric acid. Add LiOH to adjust the initial pH of the solution to pH=9. Using a 2-chambered cell separated by a divider, electrolyze the solution as described for Example 1 at a current density of 15 mA/cm$^2$. Analyze by HPLC, as described above, to determine the yield (80%) and the ratio of 3-exomethylene to 3-methyl compound (20:1) in the product mixture.

EXAMPLE 5

Prepare an aqueous electrolysis solution of 50 g/L of glutaroyl 7-ACA and 0.5M boric acid. Add LiOH to adjust the initial pH of the solution to a pH=9. Using a 2-chambered cell separated by a divider, electrolyze the solution as described for Example 1 at a current density of 15 mA/cm$^2$. Analyze by HPLC, as described above, to determine the yield (75%) and the ratio of 3-exomethylene to 3-methyl compound (30:1) in the product mixture.

EXAMPLE 6

Prepare 20 L of an aqueous electrolysis solution of 30 g/L of 7-glutaroyl 7-aminocephalosporanic acid (glutaroyl 7-ACA) and 0.5M boric acid. Add LiOH to adjust the initial pH of the solution to 9.5. Using a 2-chambered cell separated by a divider, electrolyze the solution at a temperature of 6° to 7° C. as described for Example 1 at a current density of 15 mA/cm$^2$. (The final pH of the solution is 8.2.) Analyze by HPLC, as described above, as well as by NMR, to determine the yield (79% by HPLC, 80% by NMR) and the ratio of 3-exomethylene to 3-methyl compound (25:1 by HPLC, 37:1 by NMR) in the product mixture.

Using essentially the same procedure as described for Example 6, 20 L of 50 g/L electrolysis solution was electrolyzed to give 70% yield (by HPLC) and an 3-exo to 3-methyl ratio of 28:1 (by HPLC).

EXAMPLE 7

Chromatographic Purification of Crude Electrochemical Reduction Product

Step A—Adsorbent Resin Column preconditioning:

Combine 200 mL of XAD-16 resin (Rohm & Hass) and 1500 mL of deionized distilled water, agitate for 1 hour, then decant the water. Add 1500 mL of MeOH, agitate for 1 hour, then decant the MeOH. Load approximately 155 mL of the resin in a glass chromatography column (2.4 cm×60 cm) using 250 mL of MeOH. Elute the MeOH (flow rate=2 BV/hr.), then elute with 7 L of deionized distilled water (flow rate=8 BV/hr.). Backwash the column with 2 L of deionized distilled water and allow the resin to settle. Elute the column with 1 L of 0.5M NaCL (aqueous) (adjusted to pH=3.0 with HCl, flow rate=2 BV/hr.).

Step B—Product Purification:

Load 60 mL of a 50 g/L electrolytic reduction solution containing the crude 3-exomethylene product (prepared according to Example 5) onto the resin column of Step A (flow rate=1 BV/hr., temp.=4°–5° C.). Elute the column with 60 mL of deionized distilled water (flow rate 1 BV/hr., temp.=4°–5° C.), then with 700 mL of 0.1M NaHCO$_3$ (aqueous) (pH=7.5, flow rate and temp. as above), collecting 50 mL fractions. The fractions collected are analyzed by HPLC then acidified to pH=3.5–4.0 using dilute HCl (aqueous). (Analytical results are provided in Table 1 below.) Lyophilize the appropriate fractions to isolate the purified 3-exomethylene product (70%).

TABLE 1

| Fraction # | Fraction pH | % Recovery of 3-exo-product |
|---|---|---|
| 1 | 5.11 | 0 |
| 2 | 5.21 | 0 |
| 3 | 5.80 | 0 |
| 4 | 7.69 | 0 |
| 5 | 7.48 | 1.80% |
| 6 | 7.46 | 38.7% |
| 7 | 7.26 | 22.2% |
| 8 | 8.02 | 15.5% |
| 9 | 8.30 | 12.4% |
| 10 | 8.16 | 3.65% |
| 11 | 7.86 | 1.28% |
| 12 | 7.51 | <0.5% |
| 13 | 7.47 | <0.5% |
| 14 | 7.42 | <0.5% |

Step C—Column Regeneration:

Slurry the spent resin with 5 BV of 2% NaOH for 45–60 min., decant the aqueous solution and slurry with 5 BV of deionized distilled water for 15 min. Decant the water and slurry with 5 BV of MeOH for 45–60 min. Decant the MeOH and load the resin onto a column using 1 BV of either deionized distilled water or MeOH, then elute the column with 5 BV of deionized distilled water prior to reuse.

EXAMPLE 8

Precondition a column 120 mL of XAD-1600 resin (Rohm & Haas) via essentially the same procedure as described for Example 6, Step A, then load 50 mL of a 50 g/L electrolytic reduction solution (pH=3.0) containing the crude 3-exomethylene product (prepared according to Example 5) onto the column (flow rate=1 BV/hr., temp.=4°–5° C.). Elute with: 120 mL of deionized distilled water (pH=3.0, flow rate 1 BV/hr.); 120 mL of deionized distilled water (pH=6.0, flow rate 1 BV/hr.); 500 mL of 0.1M NaHCO$_3$ (aqueous) (pH =7.5, flow rate 1 BV/hr.), while collecting 50 mL fractions. Analyze the fractions by HPLC, then adjust to pH=3.5–4.0 using dilute HCl (aqueous). (Analytical results are provided in Table 1 below.) Lyophilize the appropriate fractions to give the purified 3-exomethylene product.

TABLE 2

| Fraction # | Fraction pH | % Recovery of 3-exo-product |
|---|---|---|
| 1 | 5.93 | 0 |
| 2 | 6.17 | 0 |
| 3 | 6.16 | 0 |
| 4 | 5.65 | 0 |
| 5 | 4.58 | 0 |
| 6 | 3.84 | 0 |
| 7 | 3.78 | 0 |
| 8 | 3.72 | 0 |
| 9 | 2.82 | 0 |
| 10 | 5.01 | 0 |
| 11 | 7.01 | 15.0% |
| 12 | 7.48 | 18.8% |
| 13 | 6.89 | 18.6% |
| 14 | 6.15 | 20.5% |
| 15 | 6.31 | 22.0% |

TABLE 2-continued

| Fraction # | Fraction pH | % Recovery of 3-exo-product |
|---|---|---|
| 16 | 6.49 | 4.17% |
| 17 | 6.75 | 0.40% |
| 18 | 7.04 | 0 |

The XAD-1600 resin is regenerated via essentially the same process as described for Example 6, Step C.

EXAMPLE 9

Step A: Electrochemical Reduction

Electrochemically reduce a solution of 1.0 kg of glutaroyl 7-ACA (50 g/L) according to the procedure described for Example 6 to give a 75% solution yield of 3-exomethylene product. Lyophilize the product solution to give the solid product.

Step B: Chromatography:

A column (115 cm×7.5 cm) was loaded with 20 L of XAD-1600 resins and preconditioned at 5° C. using essentially the same procedure as described for Example 8. Prepare a solution (15 L) of about 300 g of the 3-exomethylene product from Step A (~20 g/L in deionized distilled water), adjust to pH 3.0 with 2 L of 3.7% HCl (aqueous), and load the column (5° C.) at a flow rate of 0.5 BV/h. Elute the column sequentially with 2.5 BV of deionized distilled water (pH =3.0, flow rate 1 BV/hr.), 3.5 BV of deionized distilled water (pH =6.0, flow rate 1 BV/hr.); and finally with 4 BV of 0.5M NaHCO$_3$ (aqueous) (pH=7.5, flow rate 1 BV/hr.), while collecting fractions (each fraction is 0.25 BV). Analyze the fractions by HPLC, combine the fractions which contain the 3-exomethylene product to give a 93.2% recovery of purified 3-exomethylene compound in 23.3 L of solution (12 g/L).

Concentrate the product solution by reverse osmosis (100 Dalton membrane, pressure =32 bar, 5° C.) to give a concentrated product solution of 11 L (23.0 g/L).

A sample of the 3-exomethylene product is isolated by lyophilization. $^1$H NMR (400 MHz, CDCl$_3$): 5.30–5.23 (d of d); 5.12 (d); 4.82 (s); 4.75–4.6 (m); 3.35 (d of d); 2.24–2.18 (m); 2.12–2.05 (m); 1.77–1.68 (m).

Step C: Extractive Esterification

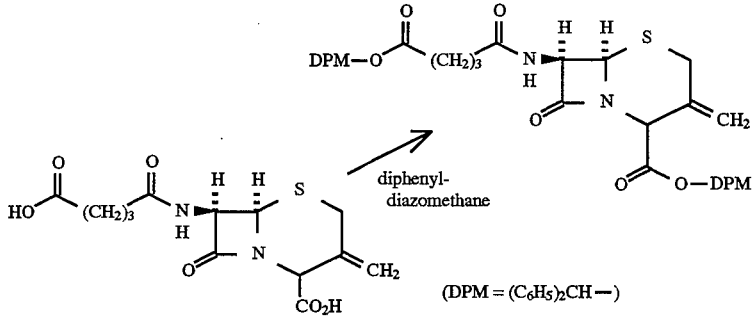

Prepare diphenyldiazomethane from benzophenone hydrazone by oxidation with a mixture of CH$_3$CO$_3$H, 1,1,3,3-tetramethylguanidine and 1% (w/v) of iodine in CH$_2$Cl$_2$. The oxidation is conducted according to the procedure described in Walker, et al., *J.C.S. Perkin I*, 2030 (1975) to give a 94% yield of diphenyldiazomethane.

Treat 1 L of the concentrated (23.3 g/L) 3-exomethylene product solution from Step B (at pH=3.0–3.4) with 2.5 equivalents of diphenyldiazomethane in CH$_2$Cl$_2$ overnight. Add an additional 10% (0.25 equiv.) of diphenyldiazomethane solution to ensure complete esterification. Concentrate the organic mixture to a residue and crystallize the residue from i-PrOH to give an 88% yield of the 3-exomethylene bis-diphenylmethyl ester (bis-DPM) product. The purity of the bis-DPM ester product is >97%. $^1$H NMR (400 MHz, CDCl$_3$): 7.35–7.15 (m, 20H); 6.80 (d, 2H); 6.03 (d, 1H); 5.58 (m, 1H); 5.3–5.1 (m, 4H); 3.42 (d, 1H); 3.0 (d, 1H); 2.41 (t, 2H); 2.15 (t, 2H); 1.9 (m, 2H).

Step D: Ozonolysis

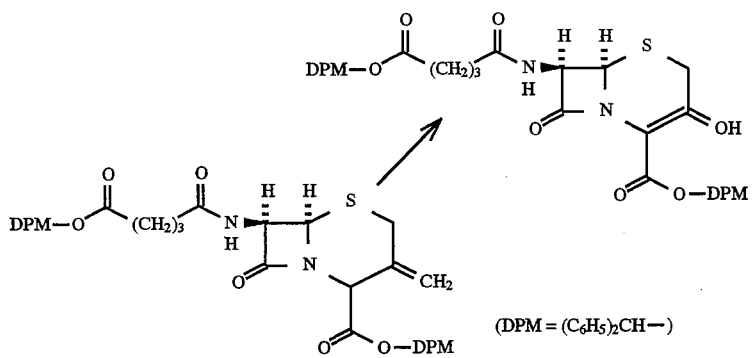

Ozonolysis of the bis-DPM ester product of Step C is carried out using standard procedures. The bis-DPM ester (70 mmol) is dissolved in EtOAc (ester concentration 80–90 g/L) and cooled to –75° C. Ozone (1.8 equiv.) is added to the mixture at –78° C. by bubbling a stream of ozone in $O_2$ through the stirred solution. The resulting mixture is stirred at –75° C. for 35–45 min. then treated with $P(OC_2H_5)_3$ (to reduce the resulting ozonide intermediate) to give a 90% yield of the 3-hydroxy cephem product.

Step E: Reduction to 3-Hydroxycepham

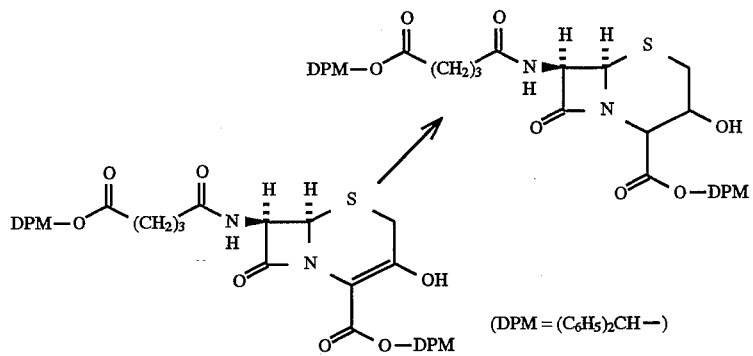

Reduce the 3-hydroxycephem product of Step D by treating with $NaBH_4$ and HOAc in a mixture of $CH_2Cl_2$ and MeOH at –50° C. for 20 min. Isolate the product to give a 60–70% yield of 7-N-glutaroyl-3-hydroxycepham bis-DPM ester.

Step F:

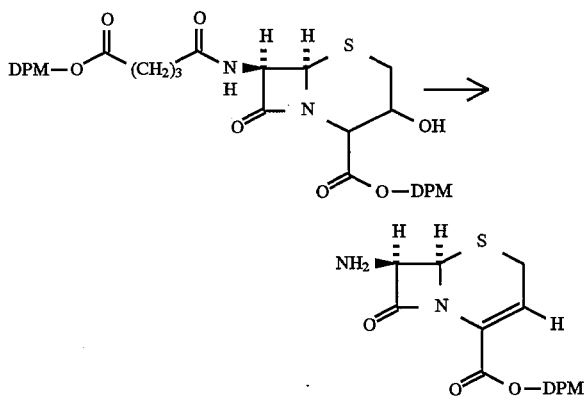

The 7-N-glutaroyl-3-hydroxycepham bis-DPM ester product of Step E is converted to 7-amino-3-desaectoxymethyl-cephalosporanic acid DPM ester (7-ADMCA DPM. ester) via essentially the same procedure as described in Yoshioka, et al., *Pure & Appl. Chem.*, 59, (No. 8) 1041–1046 (1987). The Yoshioka, et al., process is for conversion of a 7-N-phenylacetyl DPM ester to 7-ADMCA DPM ester, and is substantially the same as the process described In Reaction Scheme 3, Steps E and F, shown above. The 7-ADMCA DPM ester product is isolated in 70–80% yield and can be analyzed by HPLC (Brownlee RP18 column, diode array detector at 220 nm, eluant—65% $CH_3CN$/35% aqueous phosphate buffer (0.02M, pH=4.2), flow rate 2.0 mL/min.) $^1H$ NMR (:300 MHz, $CDCl_3$): 7.5–7.4 (m, 2H); 7.:38–7.2 (m, 8H); 6.95 (s, 1H); 6.6 (d of d, 1H); 4.85 (d of d, 2H); 3.65–3.:35 (m, 2H); 1.76 (br s, 2H).

EXAMPLE 10

The extractive esterification of Example 9, Step B can be carried out on a 40–50 g/L solution of the 3-exomethylene starting material. At such higher concentrations the reaction proceeds more rapidly (it is complete in 6 to 7 hours) and requires less diphenyldiazomethane (typically 2.5 equivalents).

EXAMPLE 11

Prepare an aqueous electrolysis solution of 10 g/L of glutaroyl 7-ACA and 0.2M boric acid. Add LiOH to adjust the initial pH of the solution to pH=9. Using a lead cathode (working electrode) in a 2-chambered cell separated by a divider, electrolyze the solution as described for Example 1 at a current density of 24 mA/cm$^2$. A total of 1200 C of charge was passed during the electrolysis. Analyze by HPLC, as described above, to determine the yield (54%) and the ratio of 3-exomethylene to 3-methyl compound (72:1) in the product mixture.

EXAMPLE 12

Prepare 10 mL of an aqueous electrolysis solution of 10 g/L of glutaroyl 7-ACA and 0.15M sodium phosphate buffer (pH=7). Using a tin cathode (working electrode) in a two chambered cell separated by a divider, at a temperature of 5° C. electrolyze the solution as described for Example 1 at a current density of 15 mA/cm$^2$. A total of 2016 C of charge was passed during the electrolysis. Analyze by HPLC, as described above, to determine the yield (72%) and the ratio of 3-exomethylene to 3-methyl compound (30:1) in the product mixture.

EXAMPLE 13

Prepare 10 mL of an aqueous electrolysis solution of 10 g/L of glutaroyl 7-ACA and 0.15M sodium phosphate buffer (pH=7). Using a tin cathode (working electrode) in a two chambered cell separated by a divider, at a temperature of 5° C. electrolyze the solution as described for Example 1 at a current density of 30 mA/cm$^2$. Analyze by HPLC, as described above, to determine the yield (70%) and the ratio of 3-exomethylene to 3-methyl compound (36:1) in the product mixture.

EXAMPLE 14

Prepare 10 mL of an aqueous electrolysis solution of 10 g/L of glutaroyl 7-ACA and 0.5M boric acid. Adjust the solution to pH=9.5 with LiOH. Using a tin cathode (working electrode) in a 2-chambered cell separated by a divider, at a temperature of 5° C. electrolyze the solution as described for Example 1 at a current density of 30 mA/cm$^2$. Analyze by HPLC, as described above, to determine the yield (67%) and the ratio of 3-exomethylene to 3-methyl compound (20:1) in the product mixture.

EXAMPLE 15

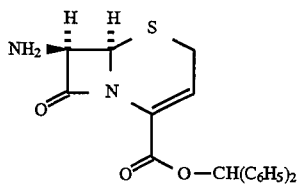

Step A: Extractive Esterification

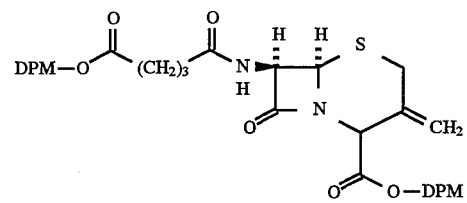

(DPM = (C$_6$H$_5$)$_2$CH—)

Add a solution of 34.2 g of diphenyldiazomethane in CH$_2$Cl$_2$ to a 1 L solution of 21.0 g (0.064 mole) of 7-β-(carboxybutanamido)-3-exomethylene-3-cepham-4-carboxylic acid. Cool the mixture to 0°–5° C. and slowly add (dropwise) 18% HCl (aqueous) to adjust to pH=3. Warm to room temperature and stir for 6 hours, then add HCl to lower the pH to 2–2.5 and stir for 1 hr. Separate the phases and extract the aqueous phase with CH$_2$Cl$_2$ (2×50 mL). Wash the combined organic phases with 500 mL of water, then concentrate in vacuo to a volume of ~70 mL. Add 300 mL of iPrOH and distill off the remaining CH$_2$Cl$_2$ at 45° C. Cool the mixture to 25° C., add seed crystals of the product and stir for 4 hrs. Cool to 0°–5° C. and stir for 0.5 hrs. Collect the product by filtration and dry in a vacuum oven at 35° C. to give 34 g of the diester product. $^1$H NMR (CDCl3, 200 MHz): 1.98 (m, 2H); 2.23 (t, 2H); 2.5 (t, 2H); 3.09–3.50 (AB quartet, 2H, J=13 Hz, J=9 Hz); 5.21–5.24 (s, 2H); 5.32 (s, 1H); 5.35 (d, 1H, J=4.3 Hz); 5.64 (d of d, 1H, J=4.3 Hz, J=9.2 Hz); 6.10 (d, 1H, J=9.2 Hz); 6.86–6.88 (s, 2H); 7.23–7.37 (br. s, 20H).

Step B: Ozonolysis

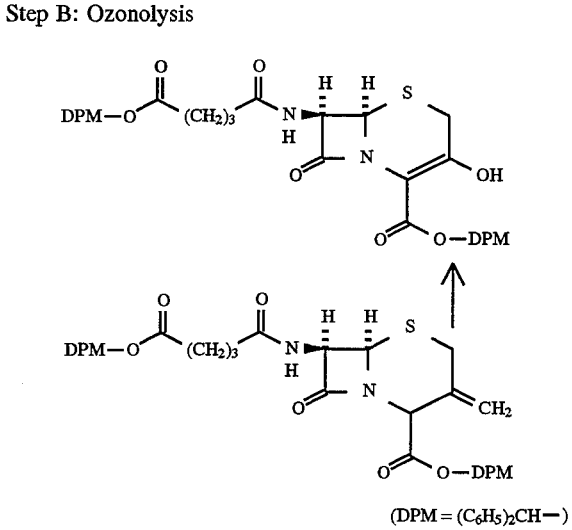

(DPM = (C$_6$H$_5$)$_2$CH—)

Dissolve 46.26 g (0.070 mole) of the bis-DPM ester product from Step A in 500 mL of EtOAc and cool to −75° C. Bubbled a stream of ozone (~2.7 mmol/min.) through the stirred solution at −75° C. for 35 min. Remove excess ozone by bubbling oxygen through the mixture for 5 minutes, then nitrogen for 15 min. Slowly add 25 mL (0.143 mole) of P(OC$_2$H$_5$)$_3$ over a 20 min. period while maintaining the temperature at <–65° C., then stir for 1 hr. Pour the mixture into 105 mL of 5% HCl (aqueous) and stir at 15°–20° C. for 1 hr. Wash the organic phase with 5% NaCl (aqueous) (2×250 mL), then concentrate in vacuo to a residue. Triturate the residue with n-pentane to give a 90% yield of the 3-hydroxy cephem product. $^1$H NMR (CDCl$_3$, 300MHz): 2.01 (m, 2H); 2.30 (t, 2H); 2.53 (t, 2H); 3.27–3.45 (AB quartet, 2H, J=17 Hz); 5.01 (d, 1H, J=4.5 Hz); 5.71 (d of d, 1H, J=4.5 Hz, J=8.5 Hz); 6.37 (d, 1H, J=8.5 Hz); 6.89–6.91 (s, 2H); 7.23–7.45 (br. s, 20H); 11.68 (s, 1H).

Step C: Reduction to 3-Hydroxycepham

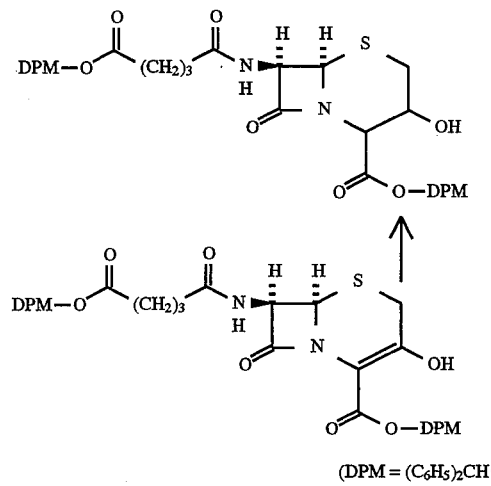

Combine 10.6 g (0.016 mole) of the 3-hydroxycephem product of Step B, 8.2 mL of glacial HOAc, 90 mL of MeOH and 180 mL of CH$_2$Cl$_2$ and cool to –55° C. Add 1.84 g (0.049 mole) of NaBH$_4$ and stir at –50° C. for 20 min. Pour the reaction mixture into a mixture of 300 mL of CH$_2$Cl$_2$ and 105 mL of 7% NaHCO$_3$ (aqueous) at room temperature and stir for 15 min. Wash the organic phase with 5% NaCl (aqueous) (2×200 mL), then concentrate in vacuo to a residue. Crystallize the residue from 100 mL of toluene by stirring at 5° C. to 12 hrs. to give 6.4 g of the product. $^1$H NMR (DMSO-d$_6$, 300 MHz); 1.96 (m, 2H); 2.23 (t, 2H); 2.48 (t, 2H); 2.61–2.98 (AB of ABX, 2H, J$_{AB}$=13.8 Hz, J$_{AX}$=10.0 Hz, J$_{BX}$=3.5 Hz); 3.32 (d, 1H, J=7.8 Hz); 4.08 (m, 1H, J=10.0 Hz, J=7.8 Hz, J=6.0 Hz); 4.84 (d, 1H, J=6.0 Hz); 5.07 (d, 1H, J=4.0 Hz); 5.53 (d or d, 1H, J=9.0 Hz, J=4.0 Hz); 6.51 (d, 1H, J=9.0 Hz); 6.87–6.92 (s, 2H); 7.2–7.4 (br. s, 20 H).

Step D—Mesylate Preparation:

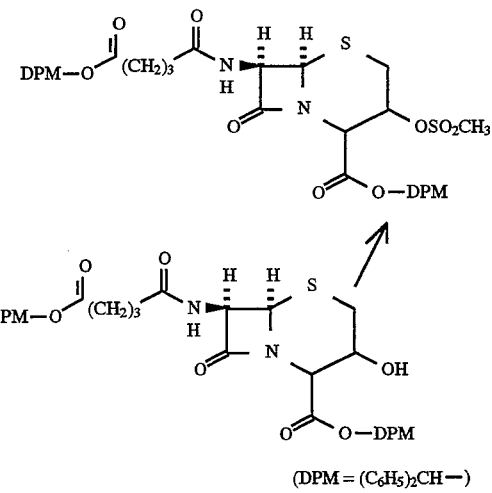

Combine 12.0 g (0.018 mole) of the product of Step C, 2.7 mL of methanesulfonyl chloride and 800 mL of CH$_2$Cl$_2$, cool to –20° C. and add 320 mL of a 1.2% solution of Et$_3$N in CH$_2$Cl$_2$ over a period of 20 min. with the temperature at <–20° C. Warm to –10° C. and stir for 1 hr., then pour the mixture into 1 L of chilled 5% NaCl (aqueous). Wash the organic phase with 5% NaCl (aqueous), then concentrate/n vacuo (temperature <35° C.) to a residue. Crystallize the residue from MeOH to give 11.4 g of the product. $^1$H NMR (CDCl$_3$, 300MHz): 2.00 (m, 2H); 2.27 (t, 2H); 2.49 (t, 2H); 2.68 (s, 3H); 2.83–3.51 (AB or ABX, 2H, J$_{AB}$=13.5 Hz, J$_{AX}$=10.5 Hz, J$_{BX}$=3.3 Hz); 5.04 (m, 2H); 5.25 (d, 1H, d=4.4 Hz); 5.50 (d of d, 1H, d=4.4 Hz, d=9.0 Hz); 6.55 (d, 1H, d=9.0 Hz); 6.89–6.95 (s, 2H); 7.2–7.4 (br. s, 20 H).

Step E—Side Chain cleavage:

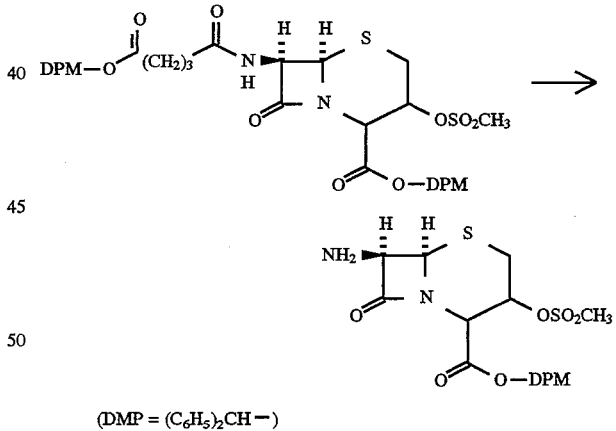

Combine 14.3 g (0.019 mole) of the product of Step D and 1.26 L of CH$_2$Cl$_2$ and cool to –50° C. Add 6.4 mL of pyridine and 8.3 g of PCl$_5$, raise the temperature to –10° C.

and stir for 2 hrs. Very slowly add 135 mL of MeOH while maintaining the temperature at <0° C. Stir for 2 hrs. at 0°–5° C., then add 1.2 L of water and add saturated Na$_2$CO$_3$ (aqueous) to adjust to pH=7. Wash the organic phase twice with 5% NaCl (aqueous), then concentrate/n vacuo at 30°–35° C. to a residue. Crystallize the residue from iPrOAc to give 6.7 g of the product. $^1$H NMR (DMSO-d$_6$, 300MHz): 3.05 (s, 3H); 3.16–3.23 (AB of ABX, 2H, J$_{AB}$=13.8 Hz, J$_{AX}$=7.2 Hz, J$_{BX}$=2.7 Hz); 4.93 (d, 1H, J=4.3 Hz); 5.15 (d, 1H, J=4.3 Hz); 5.20 (d, 1H, J=5.7 Hz); 5.37 (m, 1H, J=5.7 Hz, J=7.2 Hz, J=2.7 Hz); 6.92 (s, 1H); 7.3–7.6 (br. s, 10 H); 9.34 (br. s, 2H).

Step F—Elimination:

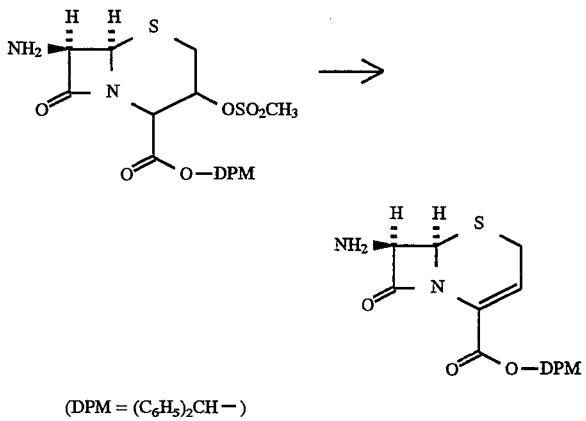

(DPM = (C$_6$H$_5$)$_2$CH—)

Combine 6.4 g (0.014 mole) of the product of Step E and 950 mL of CH$_2$Cl$_2$ and cool to –55° C. Slowly add 13.7 g of diethylamine while keeping the temperature <–50° C. Warm the mixture to –10° C. and stir for 3–4 hrs. Pour the reaction mixture into 200 mL of 10 % H$_3$PO$_4$ (aqueous), separate the layers and wash the organic phase sequentially with 5% NaCl (aqueous), 10% NaHCO$_3$ (aqueous) and 5% NaCl (aqueous). Concentrate in vacuo to a residue, then crystallize by adding 50 mL of iPrOAc and concentrating to a volume of 15–20 mL to give 4.8 g of the title compound. $^1$H NMR (CDCl$_3$, 300 MHz): 1.78 (br. s, 2H); 3.41–3.59 (AB of ABX, 2H, J$_{AB}$=19.3 Hz, J$_{AX}$=6.4 Hz, J$_{BX}$=2.7 Hz); 4.80–4.91 (d, 2H, J=5.3 Hz); 6.63 (d of d, 1H, J=6.4 Hz, J=2.7 Hz); 6.95 (s, 1H); 7.2–7.4 (br. s, 10 H).

Step G—Alternative Elimination:

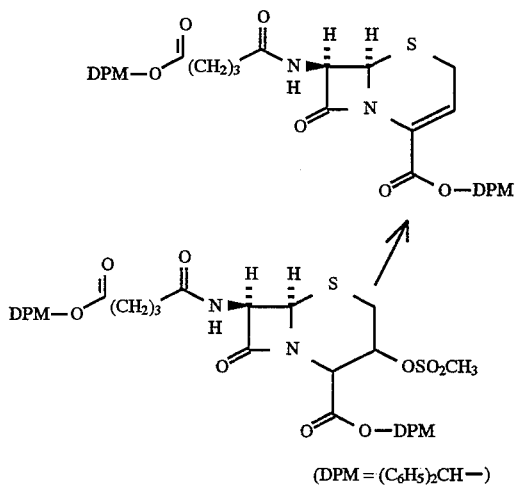

(DPM = (C$_6$H$_5$)$_2$CH—)

Combine 12.4 g (0.017 mole) of the product of Step D and 1.10 L of CH$_2$Cl$_2$, and cool to –50° C., then add 17.2 mL of diethylamine. Warm the mixture to –10° C. and star for 1 hr. Pour the cold reaction mixture into 1 L of 5 % HCl (aqueous), while keeping the temperature <10° C. Wash the organic phase with 5% NaCl (aqueous), then combine with 500 mL of water and adjust to pH=6.5 with 7% NaHCO$_3$ (aqueous). Wash the organic phase with 5% NaCl (aqueous), then concentrate in vacuo to a residue and crystallize to give 8.6 g of the product. $^1$H NMR (CDCl$_3$, 300 MHz): 2.03 (m, 2H); 2.27 (t, 2H); 2.53 (t, 2H): 3.38–3.59 (AB of ABX, 2H); 4.94 (d, 1H); 5.90 (d of d, 1H); 6.14 (d, 1H); 6.66 (d of d, 1H); 6.89–6.96 (s, 2H); 7.2–7.5 (br. s, 20H).

Step H—Alternative Side Chain cleavage:

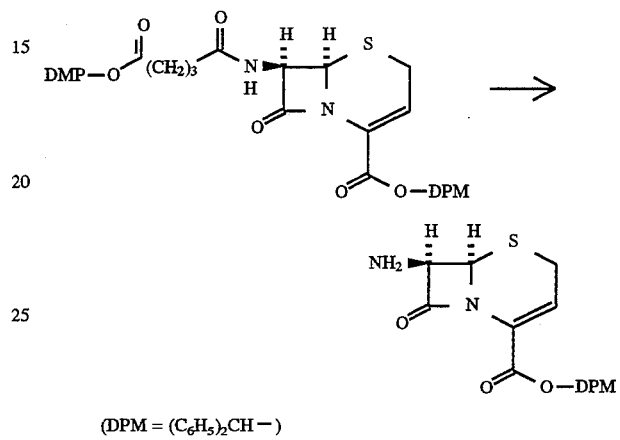

(DPM = (C$_6$H$_5$)$_2$CH—)

Combine 13.2 g (0.02 mole) of the product of Step G and 1.5 L of CH$_2$Cl$_2$, cool to –50° C., then add 6.6 mL of pyridine and 8.5 g of PCl$_5$. Very slowly add 150 mL of MeOH while maintaining the temperature at <0° C. Stir for 2 hrs. at –10° C., then add 300 mL of water and stir at <0° C. for 2 hrs. Add 7% NaHCO$_3$ (aqueous) to adjust to pH=6.5, wash the organic phase with 5% NaCl (aqueous), then concentration vacuo to a residue. Crystallize the residue from iPrOAc to give 6.6 g of the title compound.

EXAMPLE 16

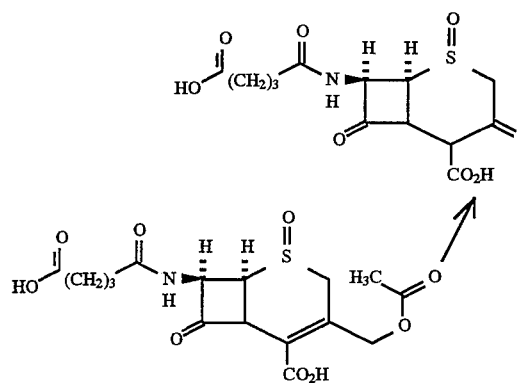

A 10 g/L solution of the sulfoxide analog of 7-glutaroyl ACA in 0.5M boric acid (aqueous) adjusted to pH 9.5 with LiOH is electrochemically reduced at 5° C., 15 mA/cm$^2$, using essentially the same procedures as described for Example 4, to give a 95% field of the 3-exomethylene product. None of the 3-methyl product was detected.

EXAMPLE 17

Prepare an aqueous electrolysis solution of 50 g/L of glutaroyl 7-ACA and electrochemically reduce the solution using a graphite felt cathode (working electrode) at a current density of 100 mA/cm² to give an 85% yield of the 3-exomethylene product.

We claim:

1. A process for preparing a compound of the formula

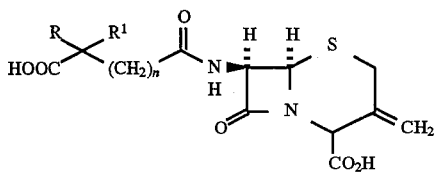

or

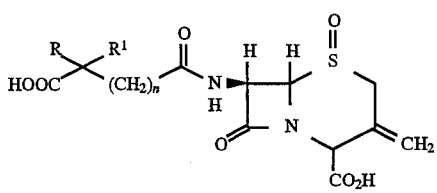

wherein: n is 2 or 3; $R^1$ is H and R is H or $NHR^2$, where $R^2$ is H or a protecting group selected from $C_6H_5CH_2OC(O)$—, $C_6H_5C(O)$— or $C_1$-$C_6$ alkoxy-C(O)—; or wherein R and $R^1$ together with the carbon atom to which they are attached comprise —C(O)—, comprising electrochemically reducing a solution of a compound of the formula

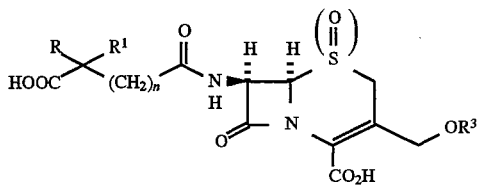

wherein: $R^3$ is $CH_3C(O)$—;

is an optional sulfoxide group; and n, R and $R^1$ are as defined above, at a concentration of 10–100 g/L, at a pH of 7–10, at a current density of 10–150 mA/cm², in a solvent containing a buffer, said solvent being selected from water, an organic solvent, or a mixture of water and a water miscible organic additive.

2. The process of claim 1 wherein the electrochemical reduction is carried out at a temperature of –20° to 20° C.

3. The process of claim 2 wherein the solvent is water and the electrochemical reduction is conducted at a temperature of 0° C. to 10° C.

4. The process of claim 3 wherein the electrochemical reduction is carried out at a pH of from 8 to 9.5, and a cathode selected from a tin, mercury or lead electrode.

5. The process of claim 4 wherein the electrochemical reduction is performed using a 2-chambered cell wherein the chambers are separated by an ion exchange membrane.

6. The process of claim 5 wherein the ion exchange membrane is a perfluorinated sulfonic acid or perfluorinated carboxylic acid ionomer membrane and wherein the membrane is permeable to cations but not permeable to anions.

7. The process of claim 1 wherein the electrochemical reduction is performed using a 2-chambered cell wherein the chambers are separated by an ion exchange membrane.

8. The process of claim 7 wherein the ion exchange membrane is a perfluorinated sulfonic acid or perfluorinated carboxylic acid ionomer membrane and wherein the membrane is permeable to cations but not permeable to anions.

9. The process of claim 1, further comprising purification of the compound prepared by the electrochemical reduction by chromatography using a column comprising an adsorbent resin.

10. The process of claim 1 wherein the electrochemical reduction is carried out using a cathode which is selected from a titanium, indium, cadmium, lead, gallium, zinc, silver, tin, bismuth, mercury, platinum, molybdenum, niobium, tantalum, carbon, copper, iron or nickel electrode, or an electrode comprising a metal alloy selected from lead/silver alloy, copper/mercury alloy or steel.

11. The process of claim 10 wherein the cathode is titanium, indium, cadmium, mercury, lead, gallium, zinc, silver, tin, bismuth or carbon, wherein the carbon is in the form of graphite, graphite felt or reticulated vitreous carbon.

12. The process of claim 1 wherein the electrochemical reduction is carried out using a tin electrode.

13. A process for preparing a compound of the formula

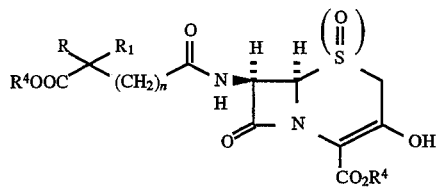

wherein: $R^4$ is diphenylmethyl;

is an optional sulfoxide group; n is 2 or 3; $R^1$ is H and R is H or $NHR^2$, where $R^2$ is H, $C_6H_5C(O)$—, $C_6H_5CH_2OC(O)$— or $C_1$-$C_6$ alkoxy-C(O)—; or R and $R^1$ together with the carbon atom to which they are attached compose —O(O)—, comprising the steps:

(a) electrochemically reducing a compound of the formula

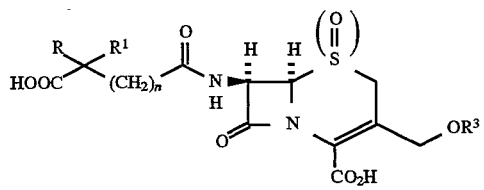

wherein: $R^3$ is $CH_3C(O)$—; and

, n, R and $R^1$ are as defined above, to form a product of the formula,

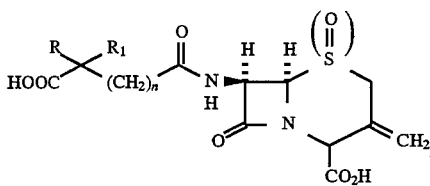

wherein $\begin{pmatrix} O \\ \| \\ \| \end{pmatrix}$, n, R and $R^1$ are as defined above, followed by chromatographic purification of the formed product on an adsorbent resin;

(b) esterifying the formed product of step (a) to form a compound of the formula

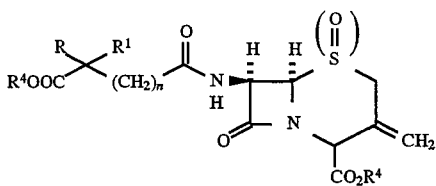

wherein $R^4$ is diphenylmethyl, and n, $\begin{pmatrix} O \\ \| \\ \| \end{pmatrix}$, R and $R^1$ are as defined above; and (c) ozonolyzing the compound of step (b).

14. A process for preparing a compound of the formula

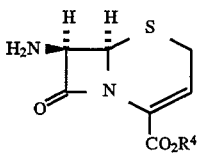

wherein: $R^4$ is diphenylmethyl, comprising the steps:

(a) electrochemically reducing a compound of the formula

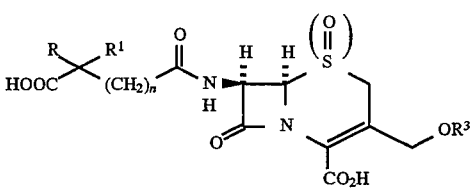

wherein: $R^3$ is $CH_3C(O)—$;

$\begin{pmatrix} O \\ \| \end{pmatrix}$ is an optional sulfoxide group; n is 2 or 3; $R^1$ is H and R is H or $NHR^2$, where $R^2$ is H, $C_6H_5C(O)—$, $C_6H_5CH_2OC(O)—$ or $C_1-C_6$ alkoxy-$C(O)—$; or R and $R^1$ together with the carbon atom to which they are attached comprise $—C(O)—$, to form a product of the formula,

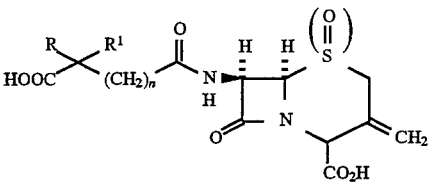

wherein $\begin{pmatrix} O \\ \| \\ \| \end{pmatrix}$, n, R and $R^1$ are as defined above, followed by chromatographic purification of the formed product on an adsorbent resin;

(b) esterifying the formed product of step (a) to form a compound of the formula

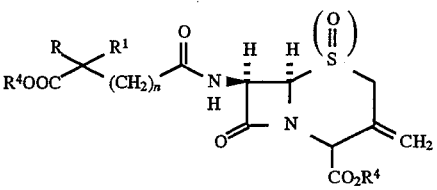

wherein $R^4$ is diphenylmethyl, and n, $\begin{pmatrix} O \\ \| \\ \| \end{pmatrix}$, R and $R^1$ are as defined above;

(c) ozonolyzing the compound of step (b) to form a product of the formula

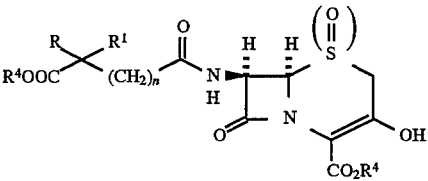

wherein $R^4$, n, $\begin{pmatrix} O \\ \| \\ \| \end{pmatrix}$,

R and $R^1$ are as defined above;

(d) reducing the product of step (c) with a hydride reducing agent to form a compound of the formula

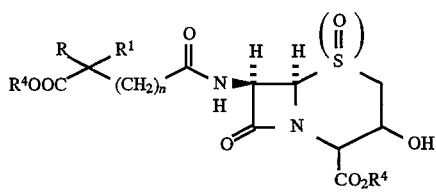

wherein $R^4$, n,

,

R and $R^1$ are as defined above;

(e) reacting the compound of step (d) with a compound of the formula P-X, wherein P is a sulfonyl activating group and X is Cl, Br or I, with a tertiary amine base to form a product of the formula

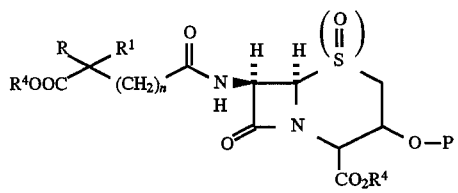

wherein P is a sulfonyl activating group, and $R^4$, n,

,

R and $R^1$ are as defined above; and (f)
  (i) treating the product of step (e) first with $PCl_5$ with a tertiary amine base and an alcohol or diol, and then with a dialkylamine base; or
  (ii) treating the product of step (e) first with a dialkylamine base and then with $PCl_5$ with a tertiary amine base and an alcohol or diol;

and where an optional

group is present, treating with $PCl_3$ to form the compound of the formula

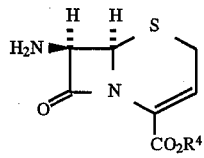

wherein $R^4$ is as defined above.

15. A process for preparing a compound of the formula

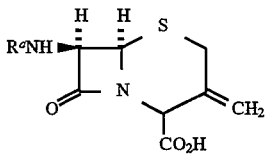

or

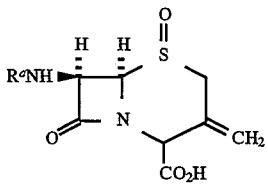

wherein: $R^a$ is H or an acyl group; comprising electrochemically reducing a solution of a compound of the formula

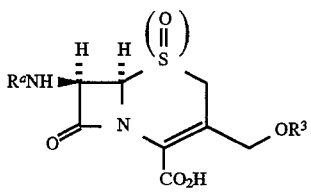

wherein: $R^3$ is $CH_3C(O)$—;

is an optional sulfoxide group; and $R^a$ is as defined above, at a concentration of 10–100 g/L, at a pH of 7–10, at a current density of 10–150 mA/cm², in a solvent containing a buffer, said solvent being selected from water, an organic solvent, or a mixture of water and a water-miscible organic additive.

16. The process of claim 15 wherein the electrochemical reduction is carried out using a tin electrode.

17. A process for preparing a compound of the formula

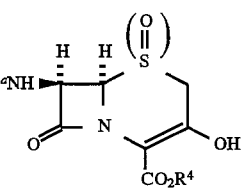

wherein: $R^4$ is diphenylmethyl;

is an optional sulfoxide group; and $R^a$ is H or acyl; comprising the steps:

(a) electrochemically reducing a compound of the formula

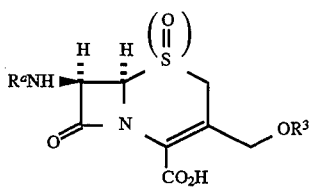

wherein: $R^3$ is $CH_3C(O)$—; and $$\begin{pmatrix} O \\ \| \\ S \end{pmatrix}$$

and $R^a$ is as defined above, to form a product of the formula

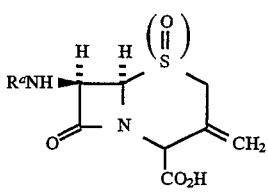

wherein $$\begin{pmatrix} O \\ \| \\ S \end{pmatrix}$$

and $R^a$ is as defined above; followed by chromatographic purification of the formed product on an adsorbent resin;

(b) esterifying the formed product of step (a) to form a compound of the formula

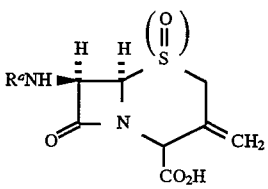

wherein $R^4$ is diphenylmethyl, and $$\begin{pmatrix} O \\ \| \\ S \end{pmatrix}$$

and $R^a$ is as defined above; and (c) ozonolyzing the compound of step (b).

18. A process for preparing compounds of the formula

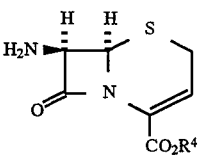

wherein: $R^4$ is diphenylmethyl, comprising the steps:

(a) electrochemically reducing a compound of the formula

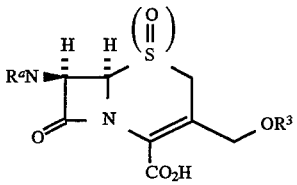

wherein; $R^3$ is $CH_3C(O)$—;

$$\begin{pmatrix} O \\ \| \\ S \end{pmatrix}$$

is an optional sulfoxide group, and $R^a$ is H or an acyl group; to form a product of the formula,

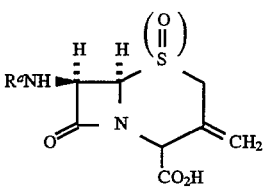

wherein $$\begin{pmatrix} O \\ \| \\ S \end{pmatrix}$$

and $R^a$ is as defined above; followed by chromatographic purification of the formed product on an adsorbent resin;

(b) esterifying the formed product of step (a) to form a compound of the formula

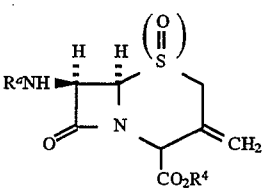

wherein $R^4$ is diphenylmethyl, and $$\begin{pmatrix} O \\ \| \\ S \end{pmatrix}$$

and $R^a$ is as defined above; and (c) ozonolyzing the compound of step (b) to form a product of the formula

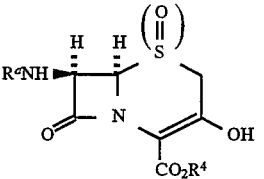

wherein $\begin{pmatrix} O \\ \parallel \end{pmatrix}$, $R^4$ and $R^a$ are as defined above;

(d) reducing the formed product of step (c) with a hydride reducing agent to form a compound of the formula

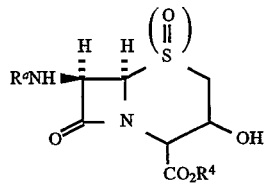
[(VIIIA)]

wherein $\begin{pmatrix} O \\ \parallel \end{pmatrix}$, $R^4$ and $R^a$ are as defined above;

(e) reacting the compound of step (d) with a compound of the formula P-X, wherein P is a sulfonyl activating group and X is Cl, Br or I, with a tertiary amine base to form a product of the formula

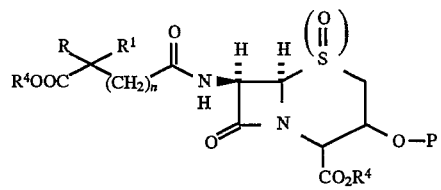
[(IXA)]

wherein P is a sulfonyl activating group, and $\begin{pmatrix} O \\ \parallel \end{pmatrix}$, $R^4$ and $R^a$ are as defined above; and (f)
  (i) treating the product of step (e) first with $PCl_5$ with a tertiary amine base and an alcohol or diol, and then with a dialkylamine base; or
  (ii) treating the product of step (e) first with a dialkylamine base and then with $PCl_5$ with a tertiary amine base and an alcohol or diol;

and where an optional $\begin{pmatrix} O \\ \parallel \end{pmatrix}$ group is present, treating with $PCl_3$ to form the compound of the formula

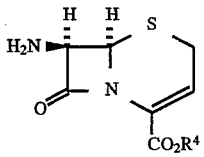

wherein $R^4$ is as defined above.

* * * * *

UNITED STATES PATENT AND TRADEMARK OFFICE
CERTIFICATE OF CORRECTION

PATENT NO. : 5,660,711
DATED : August 26, 1997
INVENTOR(S) : Derek Walker, et al Page 1 of 2

It is certified that error appears in the above-indentified patent and that said Letters Patent is hereby corrected as shown below:

In Claim 1, Column 25, lines 15-20, change

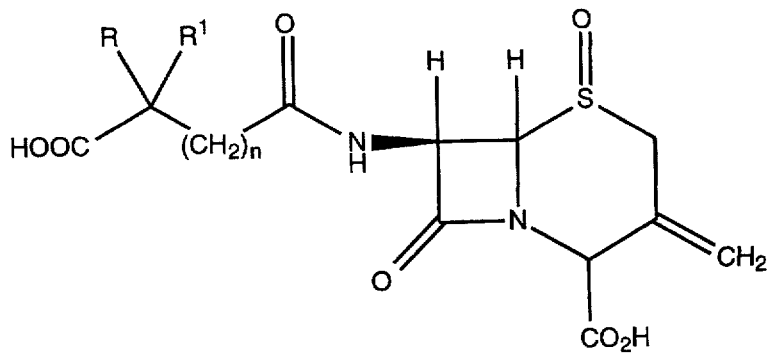

TO

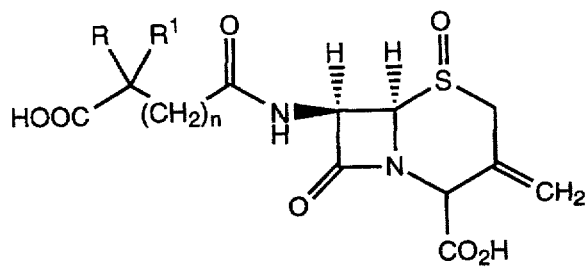

UNITED STATES PATENT AND TRADEMARK OFFICE
CERTIFICATE OF CORRECTION

PATENT NO. : 5,660,711
DATED : August 26, 1997
INVENTOR(S) : Derek Walker, et al It is certified that error appears in the above-indentified patent and that said Letters Patent is hereby corrected as shown below:

In claim 13, column 26, lines 46-47, change "compose -O(O)-" to --comprise -C(O)- --.

Signed and Sealed this

Eleventh Day of November, 1997

Attest:

BRUCE LEHMAN

Attesting Officer  Commissioner of Patents and Trademarks